United States Patent
Trieskey

(12) 
(10) Patent No.: US 6,536,518 B2
(45) Date of Patent: Mar. 25, 2003

(54) REFRIGERATION SYSTEM FOR AN ENVIRONMENTAL TEST CHAMBER

(76) Inventor: Guy T. Trieskey, 1213 E. Gemini, Tempe, AZ (US) 85283

(*) Notice: Subject to any disclaimer, the term of this patent is extended or adjusted under 35 U.S.C. 154(b) by 0 days.

(21) Appl. No.: 10/125,970

(22) Filed: Apr. 19, 2002

(65) Prior Publication Data

US 2002/0148239 A1 Oct. 17, 2002

Related U.S. Application Data

(60) Division of application No. 09/626,645, filed on Jul. 27, 2000, now Pat. No. 6,460,355, which is a continuation-in-part of application No. 09/387,315, filed on Aug. 31, 1999, now Pat. No. 6,161,391.

(51) Int. Cl.[7] ............................. F25B 7/00; F25D 17/02
(52) U.S. Cl. .................. 165/240; 62/201; 62/196.4; 62/238.7
(58) Field of Search ................... 62/196.4, 199, 62/200, 238.7, 201; 165/62, 63, 240

(56) References Cited

U.S. PATENT DOCUMENTS

| 4,336,692 A | * | 6/1982 | Ecker et al. ............. 126/615 |
| 4,645,908 A | * | 2/1987 | Jones ...................... 165/240 |
| 4,903,495 A | * | 2/1990 | Howland et al. ......... 62/196.4 |
| 5,243,825 A | * | 9/1993 | Lin .......................... 62/123 |
| 5,400,609 A | * | 3/1995 | Sjoholm et al. .......... 62/113 |
| 5,467,812 A | * | 11/1995 | Dean et al. ............... 165/62 |
| 5,894,735 A | * | 4/1999 | Misawa et al. .......... 165/240 |
| 5,983,656 A | * | 11/1999 | Tokumasu ............... 165/240 |

* cited by examiner

Primary Examiner—William E. Tapolcai
(74) Attorney, Agent, or Firm—Cahill, Von Hellens & Glazer P.L.C.

(57) ABSTRACT

An environmental test chamber provides a fast cool down to a temperature of about −125° F. and a fast heat up of an element under test. The environmental test chamber fast cool down and heat up system comprises: an environmental test chamber having a fast cool down evaporator and fast heat up condenser coil, wherein the coil is selectively coupled either to receive a hot refrigerant gas flow or to receive a sub-cooled refrigerant flow; a cascade condenser coupled to the environmental test chamber; a primary stage sub-system coupled to the cascade condenser; a secondary stage sub-system coupled to the cascade condenser; and a thermal storage unit coupled to the primary stage sub-system and to the secondary stage sub-system. Wherein the environmental test chamber has an operational temperature down to about −125° F.

3 Claims, 13 Drawing Sheets

THE REFRIGERATION CYCLE

A TO B    EVAPORATOR PRESSURE CONSTANT ENTHALPY INCREASES.

B TO C    COMPRESSOR BOTH PRESSURE AND ENTHALPY INCREASE.

C TO D    CONDENSER PRESSURE CONSTANT ENTHALPY DECREASES.

D TO A    METERING DEVICE PRESSURE DECREASES ENTHALPY CONSTANT

CONVENTIONAL CASCADE SYSTEM

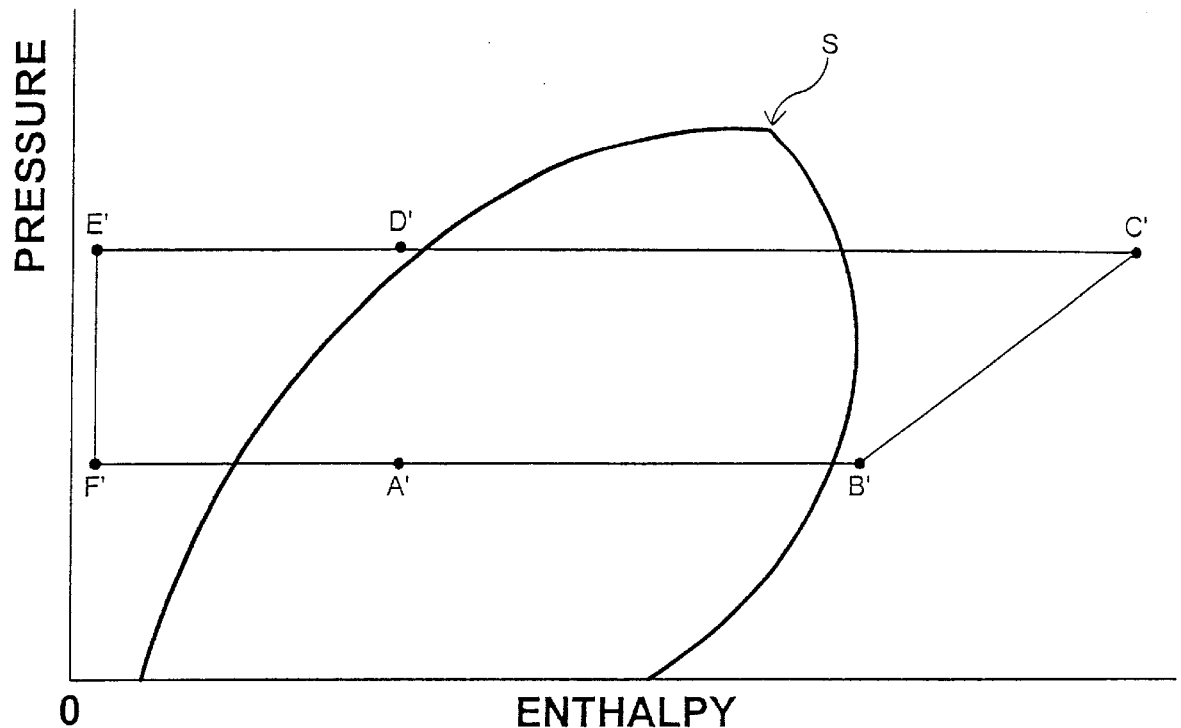

THE REFRIGERATION CYCLE NOW SUBCOOLED BY THE THERMAL STORAGE SYSTEM

POINT A' NO LONGER HAS ANY SIGNIFICANCE

F' TO B'  EVAPORATOR
 PRESSURE CONSTANT ENTHALPY INCREASES.

B' TO C'  COMPRESSOR
 BOTH PRESSURE AND ENTHALPY INCREASE.

C' TO D'  CONDENSER
 PRESSURE CONSTANT ENTHALPY DECREASES.

D' TO E'  THERMAL STORAGE SYSTEM (SUBCOOLING)
 PRESSURE CONSTANT ENTHALPY DECREASES.

E' TO F'  METERING DEVICE
 PRESSURE DECREASES  ENTHALPY CONSTANT.

FIGURE 3

CASCADE SYSTEM WITH THERMAL STORAGE

| DEMAND FROM TEMPERATURE CONTROLLER | SOLENOID VALVE #1 322 | SOLENOID VALVE #2 324 | SOLENOID VALVE #3 332 | SOLENOID VALVE #4 364 | SOLENOID VALVE #5 352 | REMARKS |
|---|---|---|---|---|---|---|
| FULL COOLING 100% OUTPUT | OPEN | CLOSED | OPEN | CLOSED | CLOSED | MAXIMUM COOLING OF LOAD |
| PARTIAL COOLING 0-100% OUTPUT | PROPORTIONED 0-100% OUTPUT | CLOSED | CLOSED | OPEN | CLOSED | TEMPERATURE OF LOAD MAINTAINED |
| HEATING MODE | CLOSED | OPEN | CLOSED | OPEN | OPEN | HEAT ADDED TO LOAD BEGIN RECHARGING OF THERMAL STORAGE UNIT |
| NO COOLING OR HEATING | CLOSED | OPEN | CLOSED | OPEN | CLOSED | THERMAL STORAGE UNIT RECHARGED |

TABLE 1

APPLICABLE TO FIGURE 5

FIGURE 9

| DEMAND FROM TEMPERATURE CONTROLLER | SOLENOID VALVE #1 | | SOLENOID VALVE #2 | | SOLENOID VALVE #3 | | SOLENOID VALVE #4 | | SOLENOID VALVE #5 PORT A TO B | | SOLENOID VALVE #5 PORT A TO C | | REMARKS |
|---|---|---|---|---|---|---|---|---|---|---|---|---|---|
| | 422 | 522 | 424 | 524 | 432 | 532 | 464 | 564 | 452 | 552 | 452 | 552 | |
| FULL COOLING 100% OUTPUT | OPEN | | CLOSED | | OPEN | | CLOSED | | OPEN | | CLOSED | | MAXIMUM COOLING OF LOAD |
| PARTIAL COOLING 0-100% OUTPUT | PROPORTIONED 0-100% OUTPUT | | OPEN | | CLOSED | | OPEN | | OPEN | | CLOSED | | TEMPERATURE OF LOAD MAINTAINED |
| HEATING MODE | CLOSED | | OPEN | | CLOSED | | FIGURE 6 CLOSED FIGURE 7 OPEN | | CLOSED | | OPEN | | HEAT ADDED TO LOAD BEGIN RECHARGING OF THERMAL STORAGE UNIT |
| NO COOLING OR HEATING | CLOSED | | OPEN | | CLOSED | | OPEN | | OPEN | | CLOSED | | THERMAL STORAGE UNIT RECHARGED |

TABLE 2

APPLICABLE TO FIGURES 6 & 7

FIGURE 10

| DEMAND FROM TEMPERATURE CONTROLLER | SOLENOID VALVE #1 622 | SOLENOID VALVE #2 624 | SOLENOID VALVE #3 632 | SOLENOID VALVE #4 664 | SOLENOID VALVE #5 PORT A TO B 652 | SOLENOID VALVE #5 PORT A TO C 652 | REMARKS |
|---|---|---|---|---|---|---|---|
| FULL COOLING 100% OUTPUT | CLOSED | CLOSED | OPEN | OPEN | OPEN | CLOSED | MAXIMUM COOLING OF LOAD |
| PARTIAL COOLING 0-100% OUTPUT | PROPORTIONED 0-100% OUTPUT | CLOSED | CLOSED | OPEN | OPEN | CLOSED | TEMPERATURE OF LOAD MAINTAINED |
| HEATING MODE | CLOSED | OPEN | CLOSED | CLOSED | CLOSED | OPEN | HEAT ADDED TO LOAD BEGIN RECHARGING OF THERMAL STORAGE UNIT |
| NO COOLING OR HEATING | CLOSED | OPEN | CLOSED | OPEN | OPEN | CLOSED | THERMAL STORAGE UNIT RECHARGED |

TABLE 3

APPLICABLE TO FIGURE 8

FIGURE 11

TABLE 4

TABLE 5

REFRIGERATION SYSTEM FOR AN ENVIRONMENTAL TEST CHAMBER

RELATED APPLICATION

This patent application is a Division of 09/626,645 filed Jul. 27, 2000, now U.S. Pat. No. 6,460,355, which is a Continuation-in-part to U.S. patent application Ser. No. 09/387,315, filed Aug. 31, 1999, now Pat. No. 6,161,391 entitled "An Environmental Test Chamber Fast Cool Down System And Method Therefor" in the name of the same inventor and the contents of the parent are incorporated herein by reference.

BACKGROUND OF THE INVENTION

1. Field of the Invention

This invention relates to environmental test chamber heating and cooling systems, and more specifically, to an improved system for cooling and heating environmental test chambers using a lower capacity, smaller footprint, refrigeration and heating system in combination with thermal storage.

2. Description of the Related Art

Environmental test chambers subject components within them to a variety of physically challenging test conditions. These test conditions can include acceleration tests, sand or water tests, and temperature tests. The temperature tests can consist of not only extremes of heat and cold, but also tests of large temperature changes in very short periods of time. A typical environmental test chamber system for imposing large temperature changes in very short periods of time may comprise a single or twin section insulated environmental test chamber, and coupled to the environmental test chamber, a large capacity refrigeration system. A large capacity environmental test chamber system is capable of imposing a temperature change from +150° C. to −65° C. in less than five minutes, and reducing the temperature to −73° C. Additionally, slower tests utilizing temperature ramp rates of five, ten, or 20° C. per minute, also within this field, still have large system capacity requirements.

A more complete explanation of environmental test methods and standards is detailed in: the Electronics Industries Association's, (EIA) JEDEC JESD22 group of specifications; Military Specifications Mil-Std 202, Mil-Std 750, Mil-Std 810, and Mil-Std 883; and the IEC pub 68 IEC Standards, all of which are incorporated herein by reference.

The physical plant requirements to produce these temperature changes, whether the very fast temperature ramp rate or the slower ramp rates, are very substantial. A large tonnage refrigeration and/or heating system is required, and the physical size of such a large capacity refrigeration and heating system is correspondingly large. A large tonnage refrigeration and heating system also has substantial energy requirements while it is in operation. An additional problem with conventional environmental test chamber systems is that the temperature transient, from the hot extreme to the cold extreme, for cyclic testing may be very broad i.e. −65° C. to +150° C. In order to subject the item under test to the desired temperature transition, the item under test in an environmental test chamber system must either: (1) be physically moved from a first pre-heated hot chamber into a second pre-cooled cold chamber, or visa versa, a physical transition that requires two separate and insulated chambers which results in a system with a double size facilities footprint; or (2) for a single chamber environmental test chamber system, the refrigeration and heating system must be larger yet to enable the sudden heat transfer of the item under test's heat load.

Therefore, a need existed for an improved environmental test chamber refrigeration and heating system that has the requisite temperature transition capabilities utilizing a smaller capacity refrigeration and heating system for single chamber environmental test chambers. Another need existed for an improved environmental test chamber refrigeration and heating system that has the requisite temperature transition capabilities utilizing a smaller capacity refrigeration and heating system for dual chamber environmental test chambers. A further need existed for an improved environmental test chamber refrigeration and heating system having only one insulated environmental chamber thereby eliminating the physical movement of an item under transition temperature testing and also providing a reduced facilities footprint. Yet a further need existed for an improved environmental test chamber refrigeration and heating system having a substantial improvement in energy usage efficiency.

SUMMARY OF THE INVENTION

It is an object of the present invention to provide an improved environmental test chamber refrigeration and heating system that has the requisite temperature transition is capabilities while utilizing a smaller capacity refrigeration and heating system for single chamber environmental test chambers.

It is another object of the present invention to provide an improved environmental test chamber refrigeration and heating system that has the requisite temperature transition capabilities while utilizing a smaller capacity refrigeration and heating system than would otherwise be required for dual chamber environmental test chambers.

It is a further object of the present invention to provide an improved environmental test chamber refrigeration and heating system having only one insulated environmental chamber thereby eliminating the physical movement of an item under transition temperature testing and also providing a reduced facilities footprint.

It is yet a further object of the invention to provide an improved environmental test chamber refrigeration and heating system having a substantial improvement in energy usage efficiency.

The foregoing and other objects, features, and advantages of the invention will be apparent from the following, more particular, description of the embodiments of the invention, as illustrated in the accompanying drawings.

In the description of the present invention; the following definitions will be used for the respective terms:

Coil: A coil is a heat exchanger that transfers heat; it can be an evaporator, condenser or a reheat heat exchanger depending on the direction of heat flow at the time of use and in the phase change of the refrigerant.

Condenser: In a condenser the refrigerant changes from a vapor to a liquid, lowering it's heat content in the process.

Evaporator: In an evaporator the refrigerant changes from a liquid to a vapor, raising it's heat content in the process.

Reheat Heat Exchanger: In a reheat heat exchanger the refrigerant lowers it's heat content without changing phase. In the use of a reheat heat exchanger herein it is first a condenser then as the chamber warms above the condensing temperature of the refrigerant it can only deliver sensible heat from the refrigerant.

Subcooling: Subcooling means lowering the temperature and thus the heat content of a liquid refrigerant without a change in phase.

BRIEF DESCRIPTION OF THE PREFERRED EMBODIMENTS

According to one aspect of the invention, an environmental test chamber fast cool down and heat up system is disclosed. The environmental test chamber fast cool down and heat up system comprises: an environmental test chamber having a fast cool down evaporator and fast heat up condenser coil, wherein the heat exchanger coil is selectively coupled either to receive a hot refrigerant gas flow or to receive a sub-cooled refrigerant flow; a cascade condenser coupled to the environmental test chamber; a primary stage sub-system coupled to the cascade condenser; a secondary stage sub-system coupled to the cascade condenser; and a thermal storage unit coupled to the primary stage sub-system and to the secondary stage sub-system. Wherein the environmental test chamber has an operational temperature down to about −125° F.

According to another aspect of the invention, an environmental test chamber cooling system is disclosed. The environmental test chamber cooling system comprises: an environmental test chamber having a fast cool down evaporator and fast heat up condenser coil, wherein the heat exchanger coil is selectively coupled either to receive a hot refrigerant gas flow or to receive a sub-cooled refrigerant flow; a refrigeration sub-system coupled to the heat exchanger coil; a thermal storage unit coupled to the refrigeration sub-system; wherein the environmental test chamber has an operational temperature down to about −125° F. the sub-cooled refrigerant flow cools the environmental test chamber down to about −125° F.

According to a further aspect of the invention, an environmental test chamber fast cool down and heat up system is disclosed. The environmental test chamber fast cool down and heat up system comprises: an environmental test chamber having a fast cool down evaporator and fast heat up condenser coil, wherein the heat exchanger coil is selectively coupled either to receive a hot refrigerant gas flow or to receive a sub-cooled refrigerant flow; a cascade condenser coupled to the environmental test chamber; a primary stage sub-system coupled to the cascade condenser; a secondary stage sub-system coupled to the cascade condenser; a thermal storage unit coupled to the primary stage sub-system and to the secondary stage sub-system. Wherein the environmental test chamber has an operational temperature down to about −125° F.; wherein the primary stage sub-system has up to an enthalpy change of about 104 BTUs per pound of refrigerant circulated; wherein the secondary stage sub-system has up to an enthalpy change of about 68 BTUs per pound of refrigerant circulated; and wherein the environmental test chamber further comprises a reheat exchange coil integral to the environmental test chamber.

According to yet another aspect of the invention, an environmental test chamber cooling system is disclosed. The environmental test chamber cooling system comprises: an environmental test chamber having a fast cool down evaporator and fast heat up condenser coil, wherein the heat exchanger coil is selectively coupled either to receive a hot refrigerant gas flow or to receive a sub-cooled refrigerant flow; a refrigeration sub-system coupled to the heat exchanger coil; a thermal storage unit coupled to the refrigeration sub-system; wherein the environmental test chamber has an operational temperature down to about −125° F.; and wherein the sub-cooled refrigerant flow cools the environmental test chamber down to about −125° F.; and wherein the refrigerant has an enthalpy change between about 68 to 104 BTUs per pound of refrigerant circulated.

BRIEF DESCRIPTION OF THE DRAWINGS

FIG. 3 is a pressure—enthalpy curve and sub-cooled refrigeration cycle applicable to the present invention.

FIG. 9 shows Table 1, a valve position chart for the operation of the embodiment of the present invention shown in FIG. 5.

FIG. 10 shows Table 2, a valve position chart for the operation of the embodiment of the present invention shown in FIGS. 6 and 7.

FIG. 11 shows Table 3, a valve position chart for the operation of the embodiment of the present invention shown in FIG. 8.

DESCRIPTION OF THE PREFERRED EMBODIMENTS

It should be noted in the following discussion that many items well known to those skilled in the relevant art have been left out of the conceptual drawings and conceptual explanations regarding the prior art and the present invention. These items include, without being limited to, items such as: sight glasses, filter dryers, receiver tanks, etc. Those skilled in the relevant art will therefore appreciate that these items are in fact present in an actual construction of the present invention.

Those skilled in the art will also recognize that even though this explanation discusses certain refrigerants, other refrigerants are very similar in their response and are generically speaking well within the scope of this invention. Furthermore, the exact values of a particular system, prior art or present invention, will vary with the specific system design and the starting and ending temperatures of the cooling load, etc. For example, each of the compressors in a cascade system, though typically of the same type in each high and low stage sub-system, do not possess exactly the same refrigerant flow rate.

DISCUSSION OF THE RELATED ART

Figure 1:
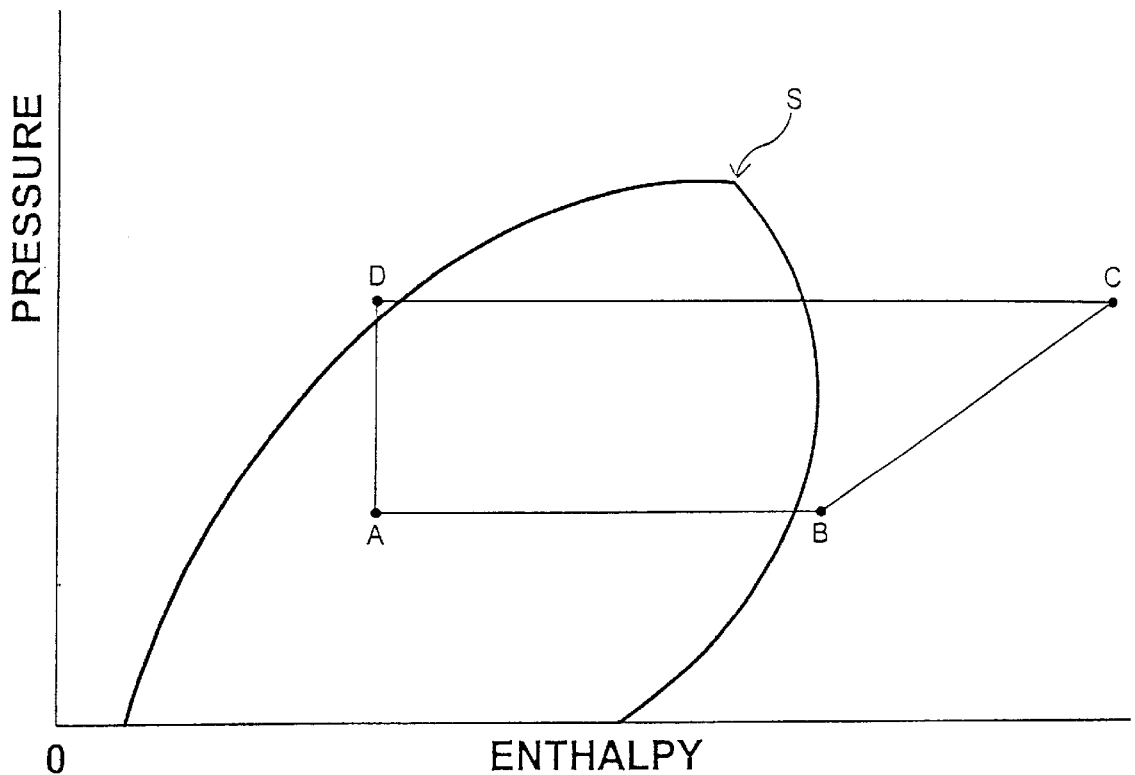
FIG. 1 is a pressure—enthalpy curve and refrigeration cycle applicable to the prior art.

Referring to FIG. 1, a saturation curve "S" and refrigeration cycle for a refrigerant applicable to the prior art is shown. The area bounded by the points A, B, C and D represents the refrigeration cycle of an ideal, prior art, refrigeration cycle. Each of the points A, B, C and D represent a point of particular pressure and temperature for a refrigerant. The actual point temperatures and pressures depend on many factors including the type of refrigerant, the component efficiencies, etc. Those skilled in the art will recognize that these factors will result in an actual, or typical refrigeration cycle, that is not as symmetrical as is this ideal example.

This ideal refrigeration cycle has the following segments:

1. Point A to B: The refrigerant passing through the evaporator absorbs heat at an essentially constant pressure thus resulting in an increase in the enthalpy of the refrigerant. During this period the refrigerant is in the saturated region for the substantial portion of this period.
2. Point B to C: The system compressor works on the refrigerant increasing its pressure. Pressure, temperature, and thus enthalpy all increase during this period. During this period the refrigerant is in the superheated vapor region.
3. Point C to D: During this period, the refrigerant passes through the condenser that removes the heat resulting from the working process. Thus, pressure is essentially constant while the enthalpy drops significantly leaving the superheat condition and entering the saturated region again. It should be noted here that while point D is barely into the sub-cooled region on this Figure, the low stage refrigerant in conventional systems typically have point D within the saturated region, and do not even have any sub-cooling effect.
4. Point D to A: As the refrigerant passes through a metering device and into the evaporator the pressure drop causes the phase change of the refrigerant from sub-cooled to a saturated liquid, thus bringing the refrigeration cycle out of the sub-cooled region almost immediately. The PSat-TSat relationship results in a substantial temperature drop of the refrigerant. During this period the phase change also contributes to the temperature drop. It should be noted that the enthalpy is essentially constant-during this period of pressure reduction. The phase change is an important part of conventional refrigeration systems.

This refrigeration cycle applies to both single loop conventional refrigeration and heating systems and also to each refrigerant in a cascade refrigeration and heating system.

Figure 2:
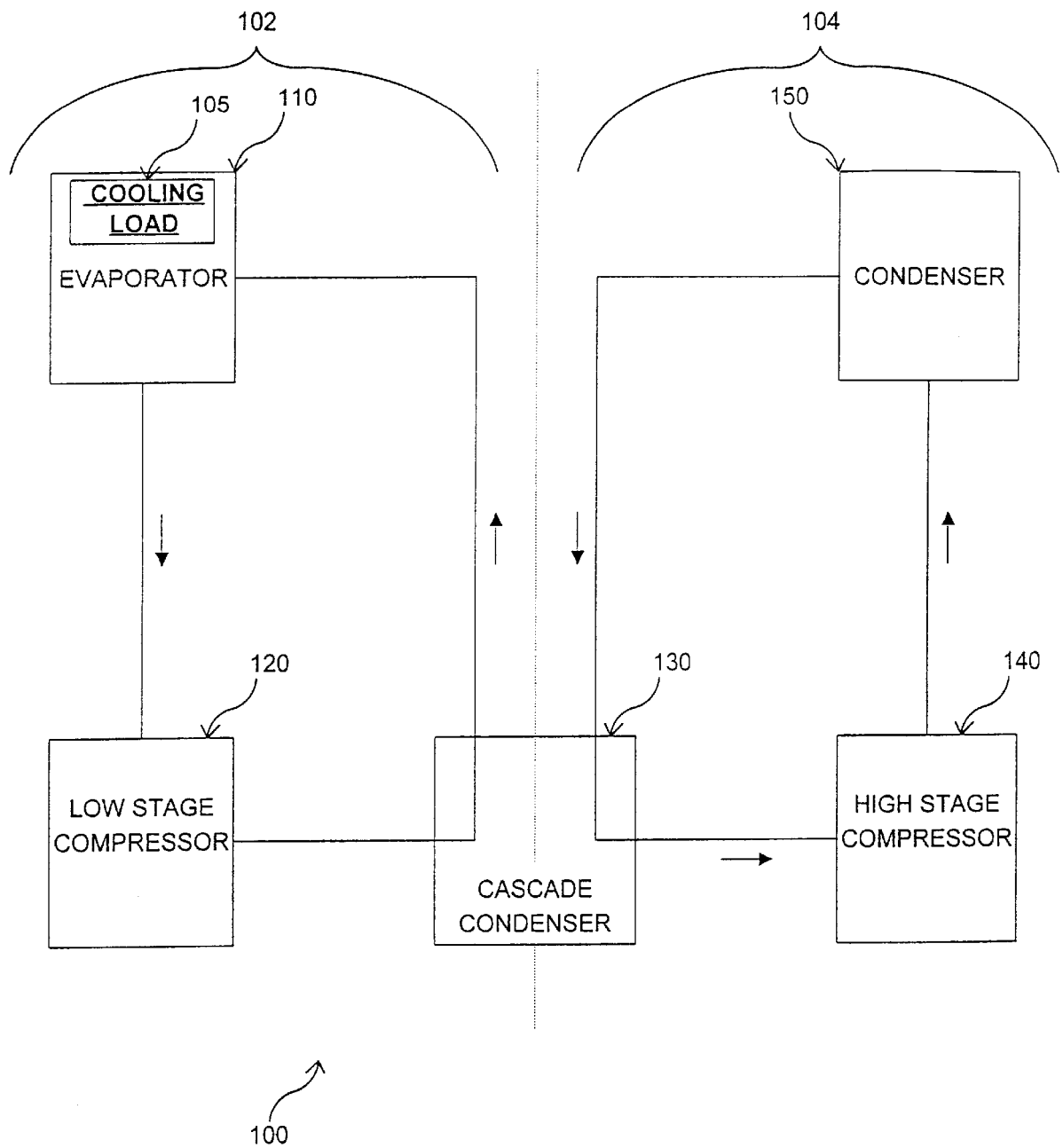
FIG. 2 is a conceptual block diagram of a prior art environmental test chamber cascade refrigeration system.

Referring to FIG. 2, a conceptual block diagram of a prior art environmental test chamber cascade refrigeration system 100 ("prior art system 100" hereinafter) is shown. The heat content of the refrigerant at various stages in the prior art system 100 will be discussed in the following. The heat content is known as enthalpy and is generally denoted by the symbol "H". Enthalpy is a state function whose change equals the heat absorbed by a system at constant pressure. Enthalpy is defined as: H=U+PV; where U is the internal energy, P is the pressure of the system and V is the volume of the system. The reference state where H=0, is defined for pure elements at 25° C. (77° F.) and one atmosphere of pressure. The enthalpy value of a refrigerant, not a pure element, is described in British Thermal Units (BTU's) per pound circulated. And, the nominal H=0 is at a temperature of −40° C. (−40° F). As this is an arbitrarily defined point, enthalpy values may be less than zero for appropriate conditions of pressure and temperature.

The prior art system 100 shown in FIG. 2 is explained with the following initial conditions:

Both low and high stage compressors 120 and 140 are operating.

It should be noted that while not shown herein, other required equipment such as fans, control equipment etc. is also functional.

The cooling load 105 is warmer than the desired temperature. Not that a single section environmental test chamber is the cooling load 105 herein, although the use of a dual section environmental test chamber would also be applicable herein.

The low stage sub-system 102 contains refrigerant R-508B. The high stage sub-system 104 contains refrigerant R-507.

Referring again to FIG. 2, liquid R-508B3 refrigerant enter the evaporator 110 with an enthalpy of approximately 14.6 BTU's per pound circulated. At the start of the cool down the R-508B refrigerant vaporizes at approximately −82° F. which increase its enthalpy to 52.0 BTU's per pound circulated. Therefore, the net work done by the low stage compressor 120 is the difference between the enthalpy of the refrigerant entering the evaporator 110 and the enthalpy of the refrigerant entering the low stage compressor 120, which equals 37.4 BTU's per pound circulated.

The heat absorbed by the low stage sub-system 102 R-508B refrigerant is delivered to the high stage sub-system 104 R-507 refrigerant via the cascade condenser heat exchanger 130. The R-507 refrigerant enters the cascade condenser heat exchanger 130 with an enthalpy of approximately 50.6 BTU's per pound circulated. The R-507 refrigerant is vaporized by the heat from the R-508B refrigerant resulting in an enthalpy increase to approximately 87.2 BTU's per pound circulated. Therefore, the net work done by the high stage compressor 140 is the difference between the enthalpy of the refrigerant entering the cascade condenser heat exchanger 130 and enthalpy of the refrigerant entering the high stage compressor 140, which equals approximately 36.6 BTU's per pound circulated. The cooling load 110 thus has its heat gradually removed until it is cooled down to the desired temperature. During this process the operating conditions of the prior art system 100 change to lower values as heat is removed from the cooling load 105 prior art system the condenser 150.

Referring again to FIG. 2, at a desired endpoint temperature of the cooling load 105 liquid R-508B refrigerant enters the evaporator 110 with an enthalpy of approximately 11.5 BTU's per pound circulated. R-508B refrigerant vaporizes at approximately −100° F. and its enthalpy increases to approximately 50.3 BTU's per pound circulated. Therefore, the net work done by the low stage compressor 120 is the difference between the enthalpy of the refrigerant entering the evaporator 110 and the enthalpy of the refrigerant entering the low stage compressor 120, which equals approximately 38.8 BTU's per pound circulated.

The heat absorbed by the low stage sub-system 102 R-508B refrigerant is delivered to the high stage sub-system 104 R-507 refrigerant via the cascade condenser heat exchanger 130. The R-507 refrigerant enters the cascade condenser heat exchanger 130 with an enthalpy of approximately 50.6 BTU's per pound circulated. The R-507 refrigerant is vaporized by the heat from the R-508B refrigerant resulting in an enthalpy increase to approximately 85.9 BTU's per pound circulated. Therefore, the net work done by the high stage compressor 140 is the difference between the enthalpy of the refrigerant entering the cascade condenser heat exchanger 130 and enthalpy of the refrigerant entering the high stage compressor 140 which equals approximately 35.3 BTU's per pound circulated. In general the foregoing is applicable to all prior art environmental cooling systems.

DISCUSSION OF THE PRESENT INVENTION THEORY AND EMBODIMENTS

Note that in the following discussion, like numbering of items and curves of FIGS. 3–8 is employed for similar items and explanations as exist in FIGS. 1–2, in accordance with the following provisions. In the case of FIG. 3, the points on the refrigeration cycle have had a prime mark, e.g. A' vs. A, added to them. And in the case of FIGS. 4–8, the numbers are series 200–600 respectively, e.g. 210 vs. 110.

Referring to FIG. 3, a saturation curve "S" and refrigeration cycle for a refrigerant applicable to the present invention is shown. The area bounded by the Points A', B', C', D', E' and F' represents the refrigeration cycle of an ideal present invention refrigeration cycle. Each of the points A', B', C', D', E' and F' represent a point of particular pressure and temperature for a refrigerant as used in the present invention. The actual point temperatures and pressures depend on many factors including the type of refrigerant, the component efficiencies etc. Those skilled in the art will recognize that these factors will result in an actual, or present invention, refrigeration cycle that is not as symmetrical as this ideal present invention example.

Figure 4:
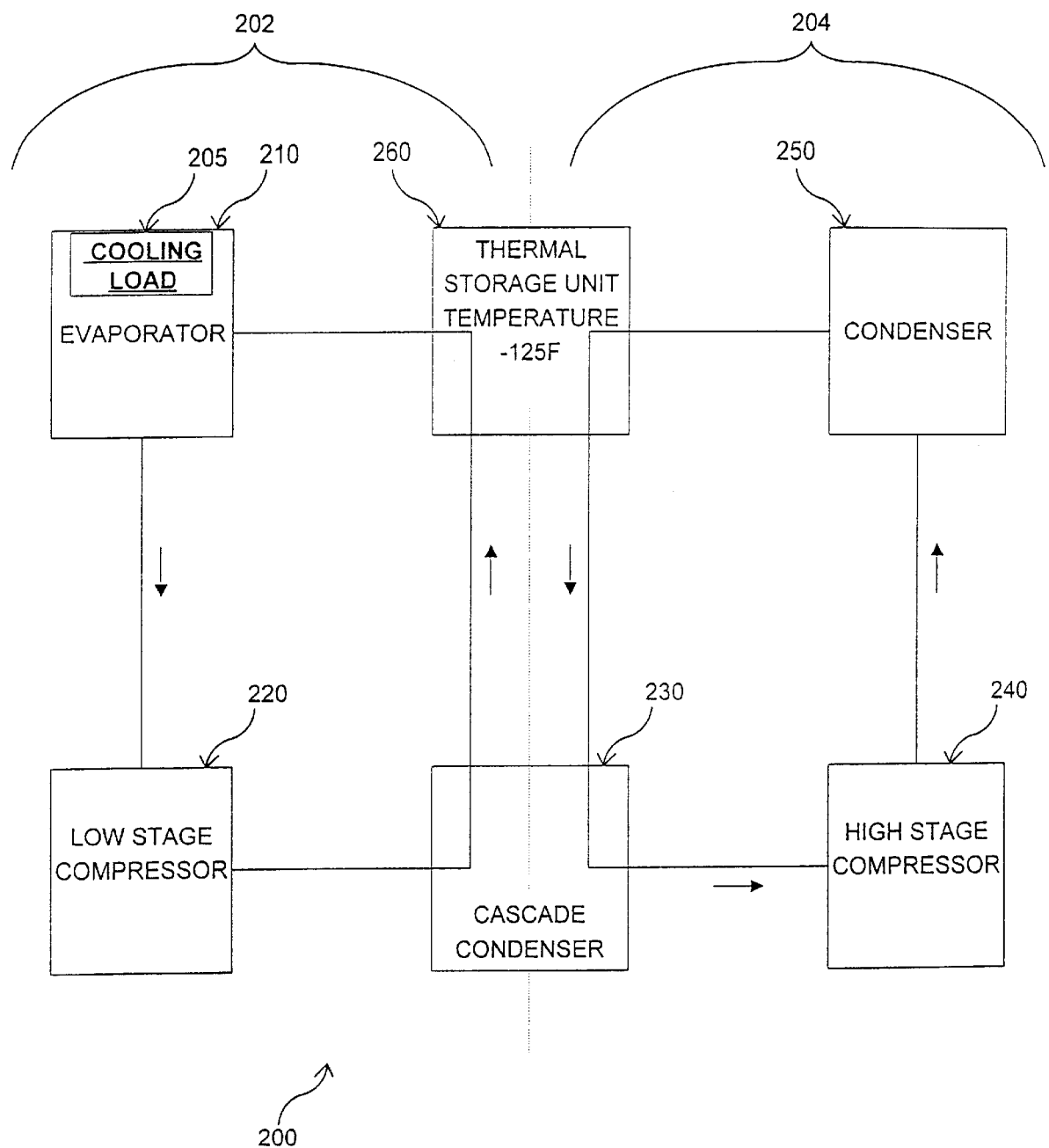
FIG. 4 is a conceptual block diagram of an environmental test chamber cascade refrigeration and heating system of the present invention.

An ideal refrigeration cycle for the present invention has the following segments:

1. Point B' to C': The system compressor works on the refrigerant increasing its pressure. Pressure, temperature and thus enthalpy all increase during this period. During this period the refrigerant is in the superheated region.
2. Point C' to D': During this period, the refrigerant passes through the condenser which removes the heat that resulted from the working process. Thus, pressure is essentially constant while the enthalpy drops significantly leaving the superheat condition and entering the saturated condition again. It should be noted here that point D is barely into the sub-cooled region. As stated previously, this is an important point in conventional refrigeration systems.
3. Point D' to E': This segment represents an important feature of the present invention. Reference to FIG. 4 will show the addition of a thermal storage unit 260 to what would otherwise be a conventional cascade system. For now, it is sufficient to state that a thermal storage unit pre-chilled to about –100° F. to about –125° F. will cause a significant drop in the enthalpy of a refrigerant at that point as is depicted on FIG. 3 from Point D' to Point E'. This additional drop in the enthalpy of the refrigerant will result in a larger amount of work done per pound of refrigerant cycled through the system.
4. Point E' to F': As the refrigerant passes through a metering device and into the evaporator the pressure drop causes a temperature reduction due to the PSat-TSat relationship, though the enthalpy remains constant. Note that the refrigerant remains in a 100% liquid form. This is an important feature of the present invention, the shifting of part of the refrigeration cycle completely into the sub-cooled region at a lower enthalpy.
5. Point F' to B': The refrigerant passing through the evaporator absorbs heat at an essentially constant pressure thus resulting in an increase in the enthalpy of the refrigerant. The refrigerant enthalpy starts well into the sub-cooled region and as heat is absorbed enters the saturated region and ends just into the superheat region. During this period a large change in enthalpy occurs.

An object of the present invention is to enable a smaller capacity, cascade or non-cascade, refrigeration and heating system, coupled to, and cooling or heating an environmental test chamber, of either the single or dual chamber variety, to achieve temperature rates of change that would otherwise require a much larger capacity refrigeration and heating system.

Figure 12:
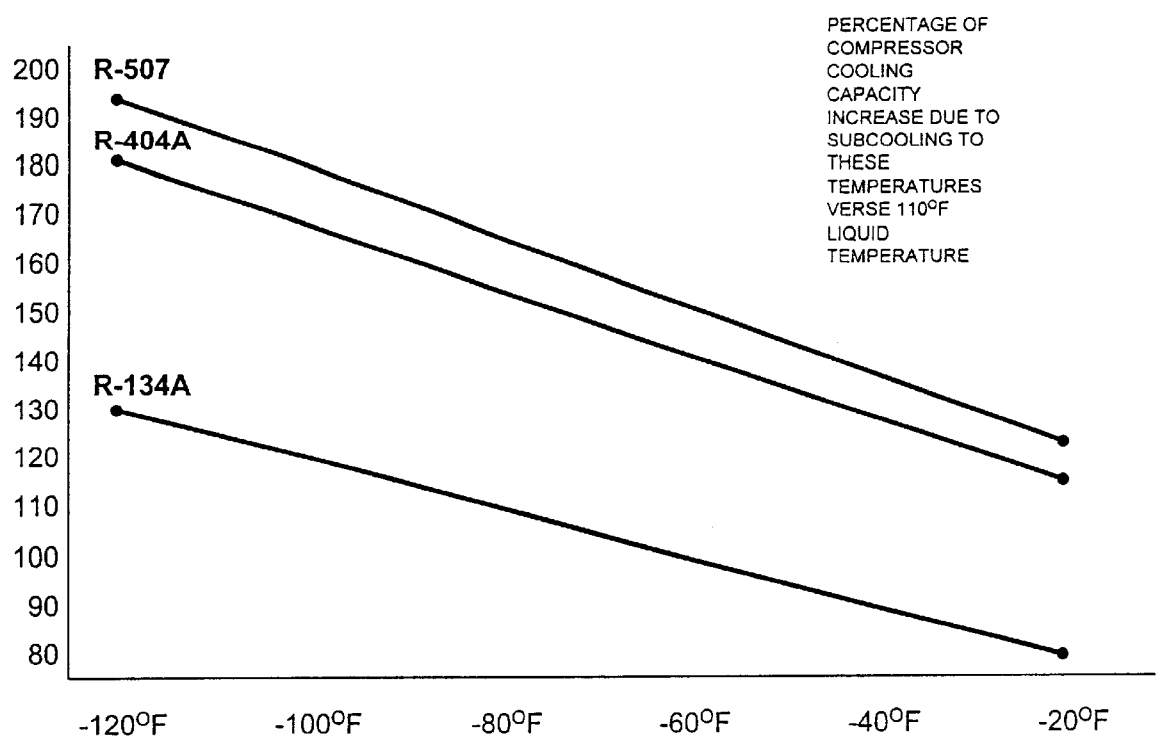
FIGS. 12 and 13 contain Tables 4 and 5, respectively, th showing the amount of compressor capacity increase obtained by subcooling the refrigerants.
Figure 13:
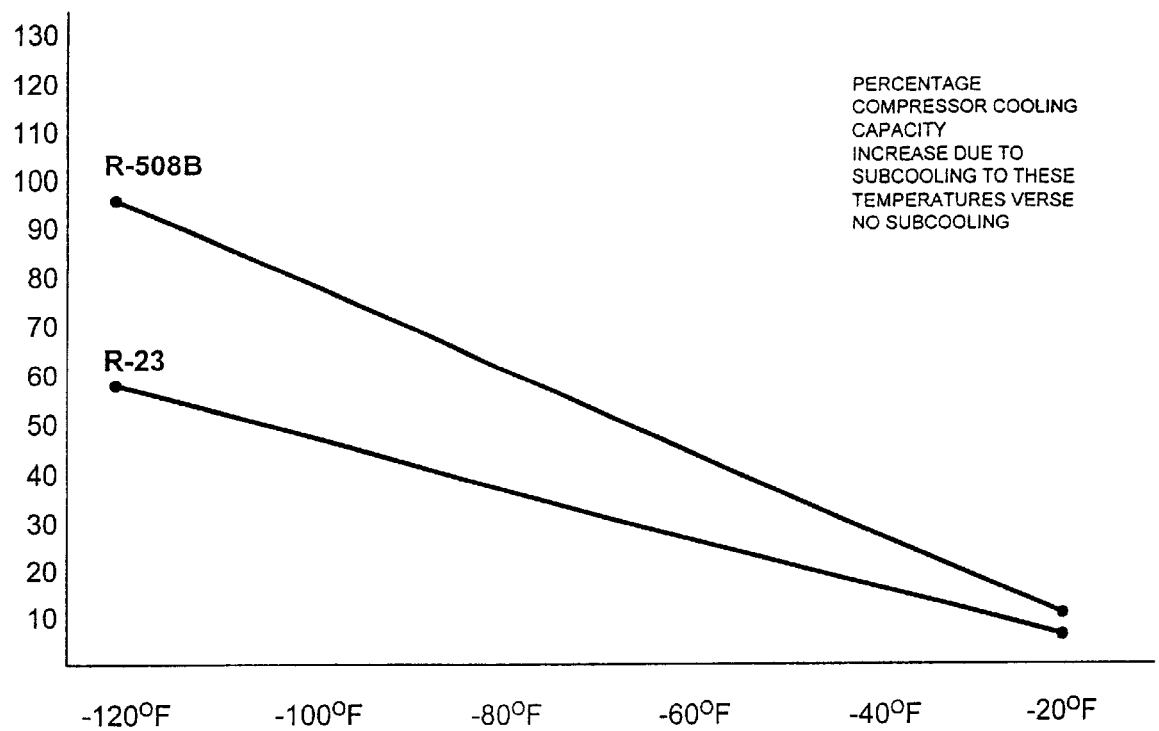

The present invention utilizes thermal transfer capacity of the system that would otherwise be wasted due to the use of a capacity control arrangement; or that would go unused due to shutting off the compressor(s) at the times that little or no thermal transfer is required. The present invention does this by having a reservoir of refrigerant, i.e. a thermal storage unit, in which the refrigerant is pre-subcooled to enhance the system's cooling performance during cool down tests, and which also serves as a load during heat up tests to maximize the heat transfer to the load being conditioned (Note: sometimes denoted as the load under test, the cooling load, etc.) This non-conventional, large size reservoir of refrigerant is much larger than any reservoir that is part of a conventional refrigeration and heating system. The reservoir stores sufficient additional pre-cooled high stage refrigerant, i.e. refrigerant that has additional heat energy pre-removed, to achieve the required temperature change rates that would otherwise require larger capacity compressor(s). Tables 4 and 5, FIGS. 12 and 13 respectively, show the amount of compressor capacity increase obtained by subcooling refrigerants in the present invention. The quantity of subcooled refrigerant is sized to provide the needs of the environmental test chamber system for the time period in which the refrigeration and heating system needs to change the temperature of the environmental test chamber and the load being conditioned within it. For example, if the compressor capacity averages a flow rate of ten pounds of refrigerant per minute, and the required temperature transition time period is 10 minutes, then the reservoir would be sized to hold 100 pounds of subcooled refrigerant which is enough refrigerant to realize a capacity increase by the compressors to achieve the needed rate of temperature change in the environmental test chamber. Conversely, if a lesser amount of subcooled refrigerant is sufficient, then the reservoir could be sized smaller; or alternatively the refrigerant need not be subcooled as much.

The present invention also utilizes heat in the liquid refrigerant that is made up into the subcooler after a cooling period by a control arrangement that begins cooling the subcooler reservoir during a desired heat up of the load being temperature conditioned. Importantly the heating process keeps a load on the refrigeration sub-system(s). This loading increases the refrigerant mass flow in the system(s) and increases hot gas temperatures, which provides more heat for the heat exchanger(s) than would otherwise be available without having a heat load to cool. This feature of the present invention allows for the maximum amount of hot gas refrigerant flow into the heat exchanger(s), when the temperature differences are large and possibly utilizing the latent heat of vaporization along utilizing the sensible heat in the refrigerant produced by the heat of compression in the compressor. During this heat up phase, the cooling of the thermal storage unit enables the system to utilize the thermal energy in the liquid refrigerant R-507 along with the electrical energy input into the compressors. The thermal energy is transferred via the hot gas into the environmental test chamber evaporator coil chamber when assisting in the heat-up of the environmental test chamber. While the environmental test chamber temperature is less than the condensing temperature of the refrigerant, the refrigerant condenses thus adding heat to the environmental test chamber that originated from the thermal energy in liquid refrigerant R-507 in the thermal storage unit. When the environmental test chamber temperature is above the condensing temperature of the refrigerant, the heat from compressor electrical energy input is the only heat added (in addition to the chamber's electric resistance heaters). The compressor(s) electrical energy is high due to reasons stated below.

The timing of this feature is important, because by waiting until the beginning of the heat up period to begin cooling the thermal storage unit for the next cycle; the load on the refrigeration system(s) is at its highest producing the largest refrigerant flow(s) and largest electrical energy draw of the compressor(s) possible, to assist in heating the environmental test chamber. If a conventional prior art system were to use hot gas to assist the chamber heat-up, it would only be able to utilize the electrical energy input into the compressor (s) which would be low as would the refrigerant(s) flow rates also Be low relative to our design due to not having a cooling load to work on. This feature further provides for energy savings due to less wattage needed from electric resistance heaters to achieve the same heat up rates that would otherwise require larger wattage electric resistance heaters.

In some embodiments, experiments have shown that the present invention system for fast cool down and heat up has less than half the amp draw of a conventional prior art system. This reduced amp draw can be a very important feature for several reasons. The reduced peak load can reduce the electric operating costs for locations that bill based on a peak draw; the reduced operating load can reduce the electric operating costs for locations that bill based on an off-peak and on-peak plan; and the reduced load can be significant when the ampacity or power availability is limited at the installation location.

The end result of the present invention is the ability to achieve required transition rate of change of temperature with smaller refrigeration equipment which makes the overall footprint of the equipment smaller, and also allows for smaller utility services which may also save energy depending on the customer's usage.

Referring to FIG. 4, a conceptual block diagram of an environmental test chamber cascade refrigeration and heating system ("system 200" hereinafter) of the present invention is shown. The heat content of the refrigerant at various stages in the system will be discussed in the following section. These are typical values obtained in an exemplary system. As those skilled in the art will recognize, actual values will vary from application to application depending on the specific equipment, refrigeration and application. The initial conditions are as follows.

Both low and high stage compressors 220 and 240 are operating.
It should be noted that while not shown herein, other required equipment such as fans, control equipment etc. is also functional.
The cooling load is warmer than the desired temperature. Note that a single section environmental test chamber is the cooling load 210 herein.
The low stage sub-system 202 contains refrigerant R-508B.
The high stage sub-system 204 contains refrigerant R-507.
The thermal storage unit 260 has been cooled to −125° F.

Those skilled in the art will recognize that even though this explanation discusses certain refrigerants, other refrigerants are very similar in their response and are generically speaking, well within this explanation. Furthermore, the exact values of a particular embodiment of the present invention will vary with the specific system design and the starting and ending temperatures of the cooling load, etc.

Referring again to FIG. 4, liquid R-508B refrigerant enters the evaporator 210. However, in the present invention, the presence of a pre-cooled thermal storage unit 260 produces an enthalpy that is much lower than the prior art system. The liquid R-508B refrigerant enters the thermal storage unit 260 with an enthalpy of 14.6 BTU's per pound circulated and the stored heat in the thermal storage unit 260 cools the refrigerant R-508B to an enthalpy of −16.4 BTU's per pound circulated. At a high heat load situation the refrigerant R-508B would be at less than a 100% liquid state and the final phase change to a 100% liquid that is sub-cooled would take place in the thermal storage unit 260. The refrigerant R-508B passing through the thermal storage unit 260 is sub-cooled to an enthalpy of approximately −16.4 BTU's per pound circulated. Note that this is 31 BTU's per pound circulated less than the same point in the prior art system 100.

The R-508B refrigerant with an enthalpy of −16.4 BTU's per pound passes through the evaporator 210. The R-508B refrigerant vaporizes at approximately −82° F., and the heat that is absorbed increases the enthalpy of the R-508B refrigerant to approximately 52.0 BTU's per pound circulated.

Therefore, the net work done by the low stage compressor 220 in combination with the thermal storage unit 260 is the difference between the enthalpy of the refrigerant entering the evaporator 210 and the enthalpy of the refrigerant entering the low stage compressor 220, which equals 68.4 BTU's per pound circulated, almost twice that of the prior art system.

The heat absorbed by the low stage sub-system 202 R-508B refrigerant is delivered to the high stage sub-system 204 R-507 refrigerant via the cascade condenser heat exchanger 230. The stored R-507 refrigerant leaves the thermal storage unit with an enthalpy of −17.2 BTU's per pound. The R-507 refrigerant next enters the cascade condenser heat exchanger 230. The R-507 refrigerant is vaporized by the heat from the R-507 refrigerant resulting in an enthalpy increase to approximately 87.2 BTU's per pound circulated. Therefore, the net work done by the high stage compressor 240 in combination with the thermal storage unit 260 is the difference between the enthalpy of the refrigerant entering the cascade condenser heat exchanger 230 and the enthalpy entering the high stage compressor 240, which equals approximately 104.4 BTU's per pound circulated. This high BTU content per pound of R-507 refrigerant circulated is almost three times greater than the prior art system 104 BTU content per pound circulated.

The cooling load 205 thus has its heat removed until it is cooled down to the desired temperature. During this process the operating conditions of the prior art system 200 change to colder values as the cooling load 205 heat is removed from the prior art system 200 via the condenser 250, and the stored heat of the thermal storage unit 260. It can be seen that the work capacity of the system 200 has been increased such that smaller system components than utilized in the prior art will enable substantially the same temperature rate of change during a cool down cycle.

Referring again to FIG. 4, at a desired endpoint temperature of the cooling load 205. The liquid R-508B refrigerant enters the thermal storage unit 260 with an enthalpy of approximately 11.5 BTU's per pound circulated where heat is removed to an enthalpy of approximately −16.4 BTU's per pound circulated. The liquid R-508B refrigerant next enters the evaporator 210. R-508B refrigerant vaporizes at approximately −100° F. and its enthalpy increases to approximately 50.3 BTU's per pound circulated. Therefore, the net work done by the low stage compressor 220 in combination with the thermal storage unit 260 is the difference between the enthalpy of the refrigerant entering the evaporator 210 and the enthalpy of the refrigerant entering the low stage compressor 220, which equals approximately 66.7 BTU's per pound circulated.

The heat absorbed by the low stage sub-system 202 R-508B refrigerant is delivered to the high stage sub-system 204 R-507 refrigerant via the cascade condenser heat exchanger 230. The thermal storage unit 260 continues to supply stored refrigerant with an enthalpy of −17.2 BTU's per pound. The R-507 refrigerant next enters the cascade condenser heat exchanger 230. The R-507 refrigerant is vaporized by the heat from the R-508B refrigerant resulting in an enthalpy increase of the R-507 refrigerant to approximately 103.1 BTU's per pound circulated. Therefore, the net work done by the high stage compressor 240 is the difference between the pre-thermal storage unit 260 enthalpy and the pre-high stage compressor 240 enthalpy, which equals approximately 85.9 BTU's per pound circulated.

DESCRIPTION AND OPERATION OF AN EMBODIMENT UTILIZING CASCADE REFRIGERATION LOOPS

Figure 5:
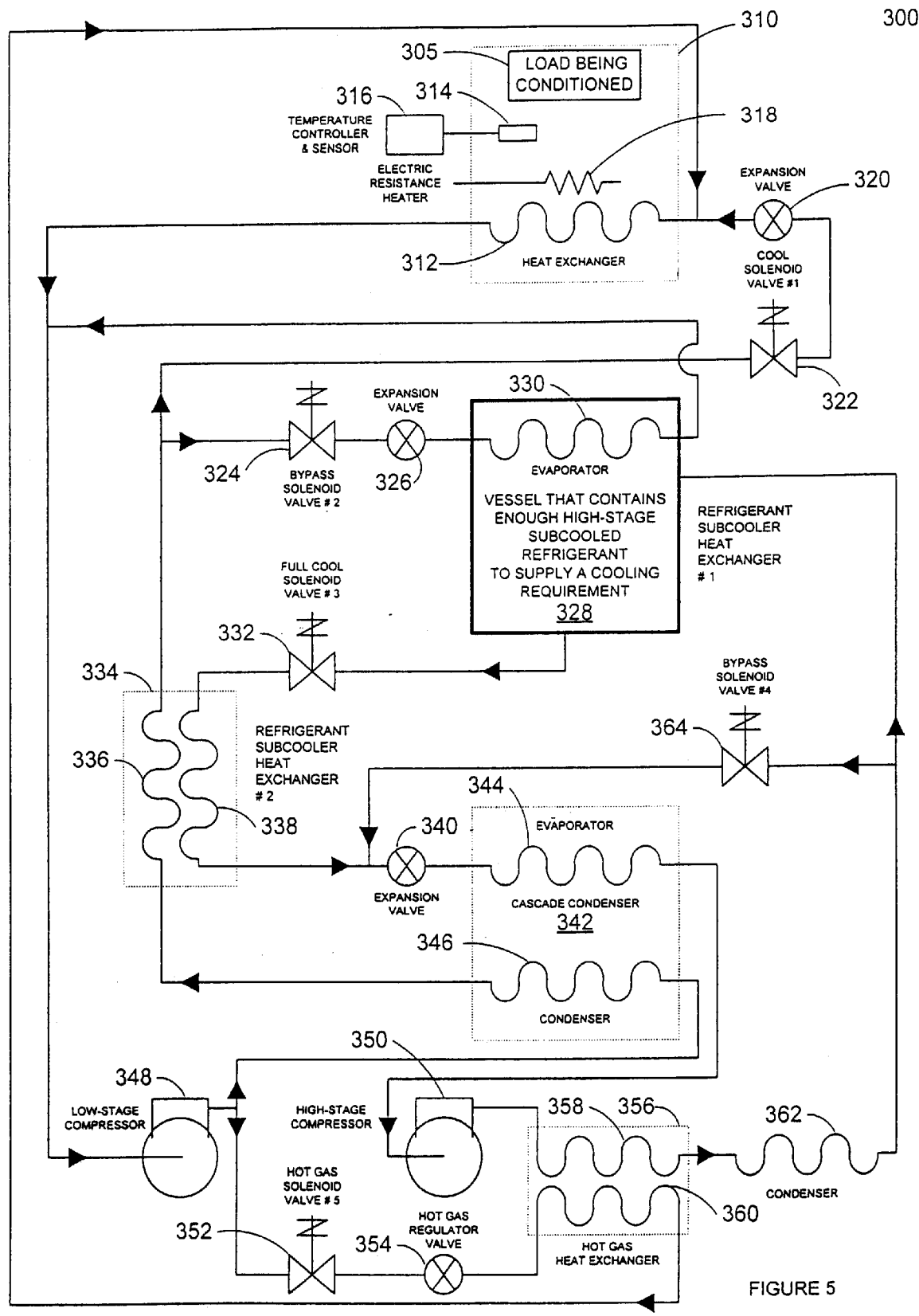
FIG. 5 is a conceptual block diagram of an embodiment of the present invention utilizing a cascade refrigeration and heating system and thermal storage of subcooled refrigerant.

Referring to FIG. 5, a conceptual block diagram of an embodiment of the present invention utilizing a cascade refrigeration and heating system and thermal storage of subcooled refrigerant is shown ("the system 300" hereinafter.) The system 300 comprises two refrigeration sub-systems, a low stage compressor sub-system and a high stage compressor sub-system. The two sub-systems are coupled together via the cascade condenser 342 for the purpose of heat transfer. The low and high stage compressor sub-systems comprises a plurality of paths for the different cooling and heating operations of the system 300. The general construction and operation of the system 300 is described below. As an aid to understanding, the solenoid valve positions for the desired system 300 operations are summarized in table 1 as shown in FIG. 9.

The system 300 initial conditions are:

1. Both low and high stage refrigeration sub-systems are running. It should be noted that while not shown herein, other required equipment such as fans, control equipment etc. is also functional.
2. The thermal storage unit 328 (subcooler #1 328) has already been cooled, the refrigerant R-507 within being sub-cooled.
3. The load being temperature conditioned 305 is warmer than the desired target temperature at the end of the conditioning cycle.
4. The low stage sub-system contains refrigerant R-508B.
5. The high stage sub-system contains refrigerant R-507.
6. A PID (Proportional-Integral-Derivative) programmable temperature controller 316 is being used to control the position of the solenoid valves 322, 324, 332, 364, and 352.
7. Electric resistance heaters 318 used for heating are off.

Those skilled in the art will recognize that even though this explanation discusses certain refrigerants, other refrigerants are very similar in their response and are generically speaking, well within this explanation. Furthermore, those skilled in the art will recognize that when a flow of refrigerant is described from one component to another, that by necessity, a physical coupling of suitable design will exist between the identified components and is implicit in the description of the refrigerant flowpath and system operation, not only in the below description but throughout this document. Additionally, although the embodiments herein show a single coil within the environmental test chamber, those skilled in the art will recognize that in fact a plurality of coils could be utilized, one as an evaporator, and one as a hot gas heat exchanger, and that such an arrangement would still be within the spirit and scope of the present invention.

Cooldown Cycle

At the start of a cooldown cycle, the temperature controller 316 signals for full cooling and opens solenoid valves #1 322 and #3 332; and simultaneously closes solenoid valves #2 324 and #4 364 to which the temperature controller 316 is coupled. Refrigerant R-508B flows out of heat exchanger coil 336, located integral to subcooler heat exchanger #2 334, and passes through solenoid valve #1 322 to which heat exchanger coil 336 is coupled. The refrigerant R-508B then passes through the expansion valve 320 that is coupled downstream of solenoid valve 322 and enter the heat exchanger coil 312 that is in turn coupled downstream of expansion valve 320. The heat exchanger coil 312 is located integral to the environmental test chamber 310, to cool the load being conditioned 305. The refrigerant R-508B is vaporized while passing through the heat exchanger coil 312 due to absorbing heat from the load being conditioned 305. The discharge from the heat exchanger coil 312 is coupled to the suction of the low stage compressor 348 where the refrigerant R-508B is compressed. The low stage compressor 348 discharges the refrigerant R-508B to the condenser coil 346, integral to the cascade condenser 342, where the refrigerant R-508B is condensed back into a liquid. The discharge of condenser coil 346 is coupled to heat exchanger coil 336, located integral to subcooler #2 334. The subcooler #2 334 further cools the refrigerant R-508B as it travels through. This completes the refrigerant R-508B flowpath during the full cool, or cooldown, cycle of the system 300.

Simultaneously with the above events for the refrigerant R-508B, the subcooled refrigerant R-507 discharges from subcooler #1 328 and through solenoid valve #3 332 to which subcooler #1 328 is coupled. The discharge from solenoid valve #3 332 is coupled to heat exchanger coil 338, integral to subcooler #2 334, where the refrigerant R-508B is subcooled. The discharged refrigerant R-507 from heat exchanger coil 338 is coupled through expansion valve 340 into the evaporator coil 344, integral to the cascade condenser 342 where the heat from the R-508B refrigerant is absorbed by the refrigerant R-507 which becomes vaporized from the absorbed heat. The discharge from the evaporator coil 344 is coupled to the high stage compressor 350 where the refrigerant R-507 is compressed. Once the refrigerant R-507 is compressed, it travels to the condenser coil 362 for removal of heat and condensing back into a liquid. The refrigerant R-507 then travels back into the subcooler #1 328. This completes the refrigerant R-507 flowpath during the full cool, or cooldown, cycle of the system 300.

Cooldown Maintaining Cycle

When the desired setpoint of the load being conditioned 305 is reached, the temperature controller 316 starts to throttle the cooling to maintain temperature at the desired setpoint. The temperature controller 316 proportions solenoid valve #1 322 on a timed cycle to maintain the desired temperature at the heat exchanger coil 312 as sensed by the sensor 314. When the demand for cooling is less than 100% the temperature controller 316 opens solenoid valve #4 364 and closes solenoid valve #3 332. The temperature controller 316 continues to proportion solenoid valve #1 322 on a timed cycle to maintain the desired temperature of the heat exchanger coil 312 and thus the load being conditioned 305. This is the cooldown maintaining cycle of the system 300.

Heat up Cycle

When a temperature increase, or heat up cycle, is desired the temperature controller 316 energizes the electric resistance heaters 318, and simultaneously opens solenoid valves #2 324, #4 364, and #5 352; while closing solenoid valve #1 322 and #3 332. Refrigerant R-508B flows out of the low stage compressor 348. Some of it flows through solenoid valve #5 352 as a high-pressure hot gas through the hot gas bypass regulator valve 354. The pressure of the refrigerant R-508B is reduced thus lowering its temperature. The refrigerant R-508B then goes into the hot gas heat exchanger 360, integral to the hot gas heat exchanger 356, where the refrigerant R-508B is reheated. The discharge from the heat exchanger coil 360 is coupled to the heat exchanger coil 312 to which the refrigerant R-508B is directed. This heats the environmental test chamber 310, and the load being conditioned 305. The refrigerant R-508B then returns to the low stage compressor 348 to be compressed again. At the same time some of hot gas refrigerant R-508B flows from the low stage compressor 348 to the condenser coil 346, integral to cascade condenser 342 where it is condensed into a liquid. It then travels through heat exchanger coil 336, integral to subcooler #2 334. The refrigerant R-508B then flows to solenoid valve #2 324 through expansion valve 326 into evaporator coil 330 subcooling the liquid refrigerant R-507 stored in subcooler 328. It is vaporized and is returned to the low stage compressor 348. This completes the heat up cycle of refrigerant R-508B by the system 300.

Simultaneously with the above events for the low stage system, liquid refrigerant R-507 flows from solenoid valve #4 364 through expansion valve 340 to evaporator coil 344, integral to cascade condenser 342. It is vaporized by the heat from the condensing R-508B in condenser coil 346. The refrigerant R-507 is then returned to the high stage compressor 350 where it is compressed, then into the hot gas heat exchanger coil 358, integral to the hot gas heat exchanger 356, heating the refrigerant R-508B, then to the condenser coil 362 where it is condensed back into a liquid. The liquid refrigerant R-507 then returns to solenoid valve #4 364. This completes the heat up cycle of refrigerant R-507 by the system 300.

Heat up Maintain/Subcool Cycle

At a predetermined temperature and/or heating demand the temperature controller 316 closes solenoid valve #5 352 and the heating process continues with only the electric resistance heaters 318 as controlled by the temperature controller 316. Solenoid valves #2 324 and #4 364 remain open in order to continue the process of subcooling the stored liquid refrigerant R-507 in the subcooler 328 for the next cooldown cycle.

DESCRIPTION AND OPERATION OF ANOTHER EMBODIMENT UTILIZING CASCADE REFRIGERATION LOOPS

Figure 6:
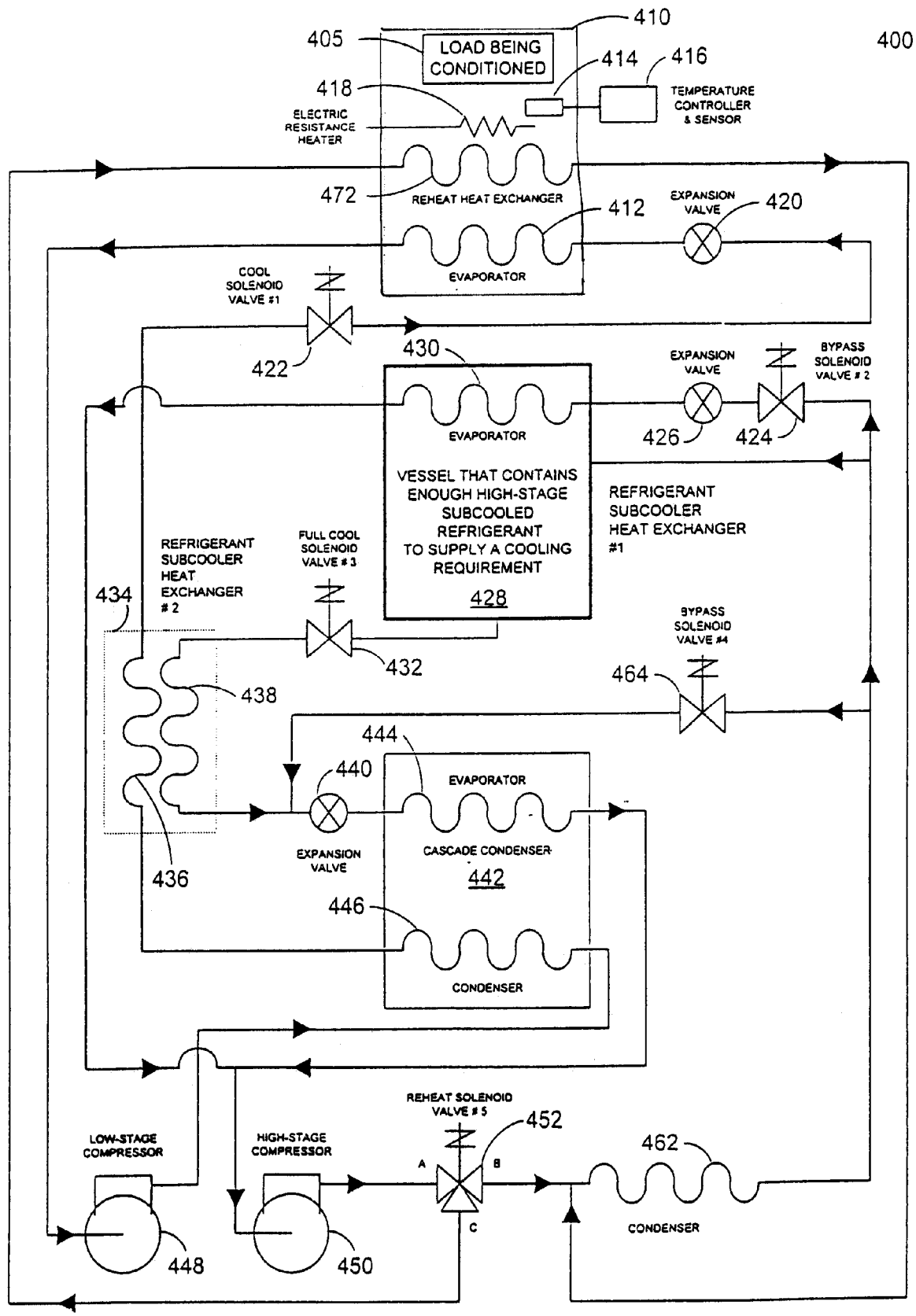
FIG. 6 is a conceptual block diagram of another embodiment of the present invention utilizing a cascade refrigeration and heating system and thermal storage of subcooled refrigerant.

Referring to FIG. 6, a conceptual block diagram of another embodiment of the present invention utilizing a cascade refrigeration and heating system and thermal storage of subcooled refrigerant is shown ("the system 400" hereinafter.) The system 400 comprises two refrigeration sub-systems, a low stage compressor sub-system, or loop, and a high stage compressor sub-system, or loop. The two sub-systems are coupled together via the cascade condenser 442 for the purpose of heat transfer. The low and high stage compressor sub-systems comprises a plurality of paths for the different cooling and heating operations of the system 400. The general construction and operation of the system 400 is described below. As an aid, the solenoid valve positions for the desired system 400 operations are summarized in table 2 as shown in FIG. 10.

This alternative system shown in FIG. 6 has as a feature that it will save electricity and wear and tear on the low stage refrigeration sub-system.

The system 400 initial conditions are:

1. Both low and high stage refrigeration sub-systems are running. It should be noted that while not shown herein, other required equipment such as fans, control equipment etc. is also functional.
2. The thermal storage unit 428 (subcooler #1 428) has already been cooled, the refrigerant within being subcooled.
3. The load being temperature conditioned 405 is warmer than the desired target temperature at the end of the conditioning cycle.
4. The low stage refrigeration sub-system contains refrigerant R-508B.
5. The high stage refrigeration sub-system contains refrigerant R-507.
6. A PID (Proportional-Integral-Derivative) programmable temperature controller 416 is being used to control the position of the solenoid valves 422, 424, 432, 464, and 452.
7. Electric resistance heaters 418 used for heating are off.

Cooldown Cycle

At the start of a cooldown cycle, the temperature controller 416 signals for full cooling and opens solenoid valves #1 422 and #3 432; and simultaneously closes solenoid valves #2 424 and #4 464 to which the temperature controller 416 is coupled. Refrigerant R-508B flows out of heat exchanger coil 436, located integral to subcooler heat exchanger #2 434, and passes through solenoid valve #1 422 to which heat exchanger coil 436 is coupled. The refrigerant R-508B then passes through the expansion valve 420 that is coupled downstream of solenoid valve #1 422 and enters the evaporator coil 412 that is in turn coupled downstream of expansion valve 420. The evaporator coil 412 is located integral tot he environmental test chamber 410, to cool the load being conditioned 405. The refrigerant R-508B is vaporized while passing through the evaporator coil 412 due to absorbing heat from the load being conditioned 405. The discharge from the evaporator coil 412 is coupled to the suction of the low stage compressor 448 where the refrigerant R-508B is compressed. The low stage compressor 448 discharges the refrigerant R-508B to the condenser coil 446, integral to the cascade condenser 442, where the refrigerant R-508B is condensed back into a liquid. The discharge of condenser coil 446 is coupled to heat exchanger coil 436, located integral to subcooler #2 434. The subcooler #2 434 further cools the refrigerant R-508B as it travels through. This completes the refrigerant R-508B flowpath during the full cool, or cooldown, cycle of the system 400.

Simultaneously with the above events for the refrigerant R-508B, the subcooled refrigerant R-507 discharges from subcooler #1 428 and through solenoid valve #3 432 to which subcooler #1 428 is coupled. The discharge from solenoid valve #3 432 is coupled to heat exchanger coil 438, integral to subcooler #2 434, where the liquid refrigerant R-508B is subcooled. The discharged refrigerant R-507 from heat exchanger coil 438 is coupled through expansion valve 440 into the evaporator coil 444, integral to the cascade condenser 442 where the heat from the R-508B refrigerant is absorbed by the refrigerant R-507 which becomes vaporized from the absorbed heat. The discharge from the evaporator coil444 is coupled to the high stage compressor 450 where the refrigerant R-507 is compressed. Once the refrigerant R-507 is compressed, it travels through solenoid valve #5 452, port A to B, to the condenser coil 463 for removal of heat and condensing back into a liquid. The liquid refrigerant R-507 then travels back into the subcooler #1 428. This completes the refrigerant R-507 flowpath during the full cool, or cooldown, cycle of the system 400.

Cooldown Maintaining Cycle

When the desired setpoint of the load being conditioned 405 is reached, the temperature controller 416 starts to throttle the cooling to maintain temperature at the desired setpoint. The temperature controller 416 proportions solenoid valve #1 422 on a timed cycle to maintain the desired temperature at the evaporator coil 412 as sensed by the sensor 414. When the demand for cooling is less than 100% the temperature controller 416 opens solenoid valve #4 464 and closes solenoid valve #3 432. The temperature controller 416 continues to proportion solenoid valve #1 422 on a timed cycle to maintain the desired temperature of the evaporator coil 412 and thus the load being conditioned 405. This is the cooldown maintaining cycle of the system 400.

Heat up cycle

When a temperature increase, or heat up cycle, is desired the temperature controller 416 energizes the electric resistance heaters 418, it simultaneously turns off the low stage compressor 448, solenoid valves #1 422, #3 432 and #4 464 are closed. The temperature controller 416 opens solenoid valve #2 424, and causes solenoid valve #5 452 to change the position of its ports. Port A is opened to port C, and port B is blocked so that refrigerant R-507 hot gas flows from the high stage compressor 450 to the reheat exchanger coil 472, integral to the environmental test chamber 410, as a high-pressure hot gas, heating the load being conditioned 405. The refrigerant R-507 then travels to the condenser coil 462 to be condensed then through solenoid valve #2 424, through expansion valve 426, through the evaporator coil 430 of subcooler #1 428, thus subcooling the stored liquid R-507 in the subcooler #1 428. Then the refrigerant R-507 travels back to the compressor 450 to be compressed again. This process, in addition to heating up the load to be conditioned 405, also begins the cool down of subcooler #1 428 in preparation for the next cooldown cycle. This completes the heat up cycle of refrigerant R-507 by the system 400.

Heat up Maintain/Subcool Cycle

At a predetermined temperature and/or heating demand the temperature controller 416 causes solenoid valve #5 452 to change the position of it's ports. Port A is opened to port B, and port C is blocked so that refrigerant R-507 continues to flow to the condenser coil 462. The heating process of the load being conditioned 405 continues with only the electric resistance heaters 418 cycling as controlled by the temperature controller 416 and the temperature sensor 414. Solenoid valve #2 424 remains open during this time to continue the process of subcooling the stored liquid refrigerant R-507 in the subcooler 428 for the next cooldown cycle.

DESCRIPTION AND OPERATION OF A THIRD EMBODIMENT UTILIZING CASCADE REFRIGERATION LOOPS

Figure 7:
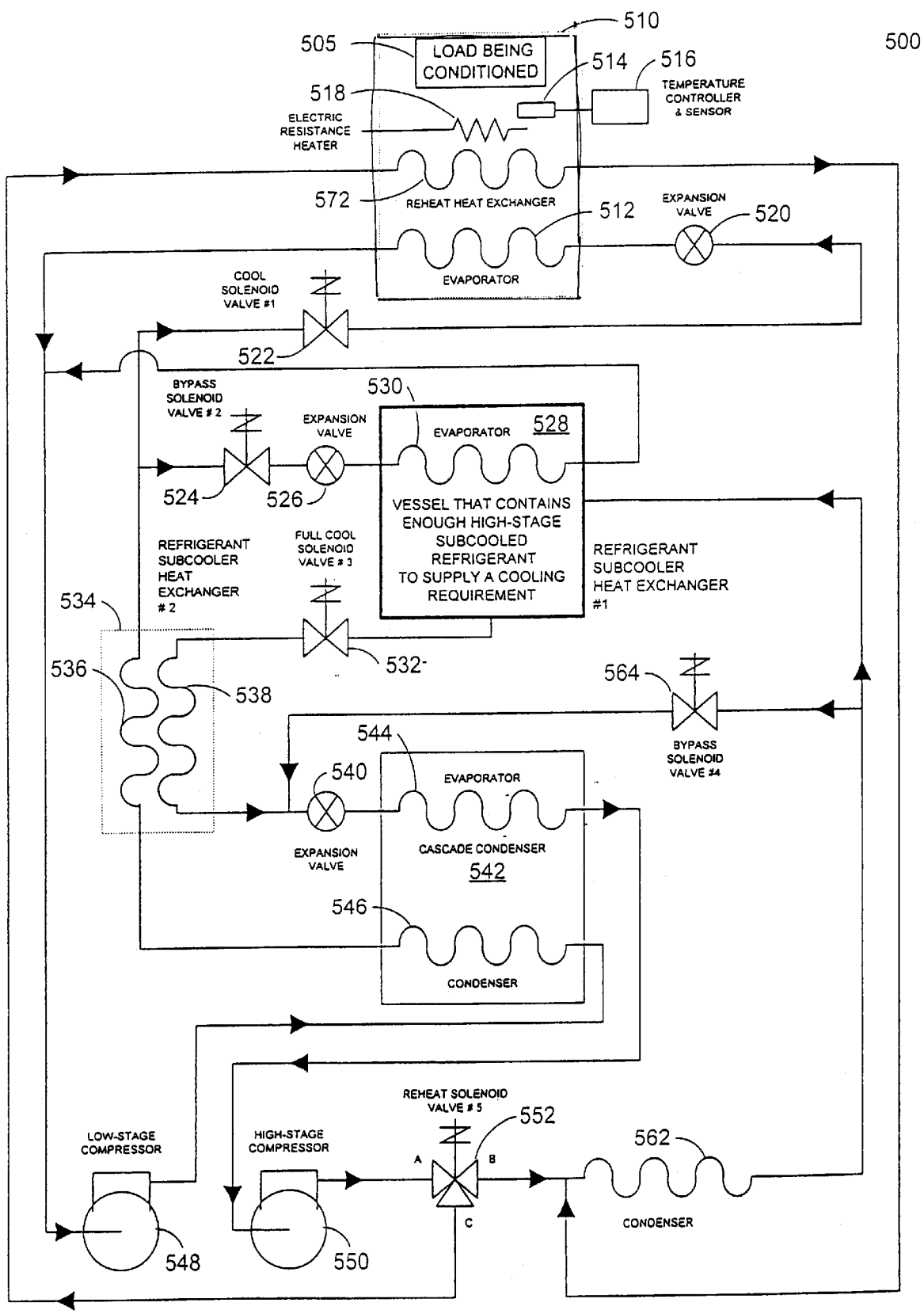
FIG. 7 is a conceptual block diagram of a third embodiment of the present invention utilizing a cascade refrigeration and heating system and thermal storage of subcooled refrigerant.

Referring to FIG. 7, a conceptual block diagram of another embodiment of the present invention utilizing a cascade refrigeration and heating system and thermal storage of subcooled refrigerant is shown ("the system 500" hereinafter.) The system 500 comprises two refrigeration sub-systems, a low stage compressor sub-system and a high stage compressor sub-system. The two sub-systems are coupled together via the cascade condenser 542 for the purpose of heat transfer. The low and high stage compressor sub-systems comprises a plurality of paths for the different cooling and heating operations of the system 500. The general construction and operation of the system 500 is described below. As an aid, the solenoid valve positions for the The system 500 initial conditions are:

1. Both low and high stage refrigeration sub-systems are running. It should be noted that while not shown herein, other required equipment such as fans, control equipment etc. is also functional.
2. The thermal storage unit 528 (subcooler #1 528) has already been cooled, the refrigerant within being subcooled.
3. The load being temperature conditioned 505 is warmer than the desired target temperature at the end of the conditioning cycle.
4. The low stage refrigeration sub-system contains refrigerant R-508B.
5. The high stage refrigeration sub-system contains refrigerant R-507.
6. A PID (Proportional-Integral-Derivative) programmable temperature controller 516 is being used to control the position of the solenoid valves 522, 524, 532, 564, and 552.
7. Electric resistance heaters 518 used for heating are off.

Cooldown Cycle

At the start of a cooldown cycle, the temperature controller 516 signals for full cooling and opens solenoid valves #1 522 and #3 532; and simultaneously closes solenoid valves #2 524 and #4 564 to which the temperature controller 516 is coupled. Refrigerant R-508B flows out of heat exchanger coil 536, located integral to subcooler heat exchanger #2 534, and passes through solenoid valve #1 522 to which heat exchanger coil 536 is coupled. The refrigerant R-508B then passes through the expansion valve 520 that is coupled downstream of solenoid valve 522 and enters the evaporator coil 512 that is in turn coupled downstream of expansion valve 520. The evaporator coil 512 is located integral to the environmental test chamber 510, to cool the load being conditioned 505. The refrigerant R-508B is vaporized while passing through the evaporator coil 512 due to absorbing heat from the load being conditioned 505. The discharge from the evaporator coil 512 is coupled to the suction of the low stage compressor 548 where the refrigerant R-508B is compressed. The low stage compressor 548 discharges the refrigerant R-508B to the condenser coil 546, integral to the cascade condenser 542, where the refrigerant R508B is condensed back into liquid. The discharge of condenser coil 546 is coupled to heat exchanger coil 536, located integral to subcooler #2 534. The subcooler #2 534 further cools the refrigerant R-508B as it travels through. This completes the refrigerant R-508B flowpath during the full cool, or cooldown, cycle of the system 500.

Simultaneously with the above events for the refrigerant R-508B, the subcooled refrigerant R-507 discharges from subcooler #1 528 and through solenoid valve #3 532 to which subcooler #1 528 is coupled. The discharge from solenoid valve #3 532 is coupled to heat exchanger coil 538, integral to subcooler #2 534, where the refrigerant R-508B is subcooled. The discharged refrigerant R-507 from heat exchanger coil 538 is coupled through expansion valve 540 into the evaporator coil 544, integral to the cascade condenser 542 where the heat from the R-508B refrigerant is absorbed by the refrigerant %–507 which becomes vaporized from the absorbed heat. The discharge from the evaporator coil 544 is coupled to the high stage compressor 550 where the refrigerant R-507 is compressed. Once the refrigerant R-507 is compressed, it travels through solenoid valve #5 552, port A to B, to the condenser coil 562 for removal of heat and condensing back into a liquid. The refrigerant R-507 then travels back into the subcooler #1 528. This completes the refrigerant R-507 flowpath during the full cool, or cooldown, cycle of the system 500.

Cooldown Maintaining Cycle

When the desired setpoint of the load being conditioned 505 is reached, the temperature controller 516 starts to throttle the cooling to maintain temperature at the desired setpoint. The temperature controller 516 proportions solenoid valve #1 522 on a timed cycle to maintain the desired temperature at the evaporator coil 512 as sensed by the sensor 514. When the demand for cooling is less than 100% the temperature controller 516 opens solenoid valve #4 564 and closes solenoid valve #3 532. The temperature controller 516 continues to proportion solenoid valve #1 522 on a timed cycle to maintain the desired temperature of the evaporator coil 512 and thus the load being conditioned 505. This is the cooldown maintaining cycle of the system 500.

Heat up Cycle

When a temperature increase, or heat up cycle, is desired the temperature controller 516 energizes the electric resistance heaters 518. The temperature controller 516 opens solenoid valves #2 524 and #4 564, and closes solenoid valves #1 522 and #3 532. The temperature controller 516 causes solenoid valve #5 552 to change the position of its ports. Port A is opened to port C, and post B is blocked so that refrigerant R-507 hot gas flows from the high stage compressor 550 to the reheat heat exchanger coil 572, integral to the environmental test chamber 5 10, as a high-pressure hot gas, heating the load being conditioned 505. The refrigerant R-507 then travels to the condenser coil 562 to be condensed, then through solenoid valve #4 564 and expansion valve 540 and into the evaporator coil 544, integral to the cascade condenser 542, thus condensing the refrigerant R-508B. Then the refrigerant R-507 travels back to the compressor 550 to be compressed again. This completes the heat up cycle of refrigerant R-507 by the system 500.

Simultaneously with the above events for the refrigerant R-507, liquid refrigerant R-508B travels through solenoid valve #2 524 through expansion valve 526 into the evaporator coil 530 of subcooler #1 528 cooling the subcooler 528. The refrigerant R-508B then returns to the low stage compressor 548 where it is compressed, then to the condenser coil 546, integral to cascade condenser 542, where it is condensed back into a liquid, through the heat exchanger coil 536, integral to subcooler #2 534 and back to solenoid valve #2 524. This completes the heating cycle of refrigerant R-508B.

Heat up Maintain/Subcool Cycle

At a predetermined temperature and/or heating demand the temperature controller 516 causes solenoid valve #5 552 to change the position of it's ports. Port A is opened to port B, and port C is blocked so that refrigerant R-507 continues to flow to the condenser coil 562. The heating process of the load being conditioned 505 continues with only the electric resistance heaters 518 cycling as controlled by the temperature controller 516 and the temperature sensor 514. Solenoid valve #2 524 remains open during this time to continue the process of subcooling the stored liquid refrigerant R-507 in the subcooler 528 for the next cooldown cycle.

DESCRIPTION AND OPERATION OF A FOURTH EMBODIMENT UTILIZING A NON-CASCADE REFRIGERATION LOOP

Figure 8:
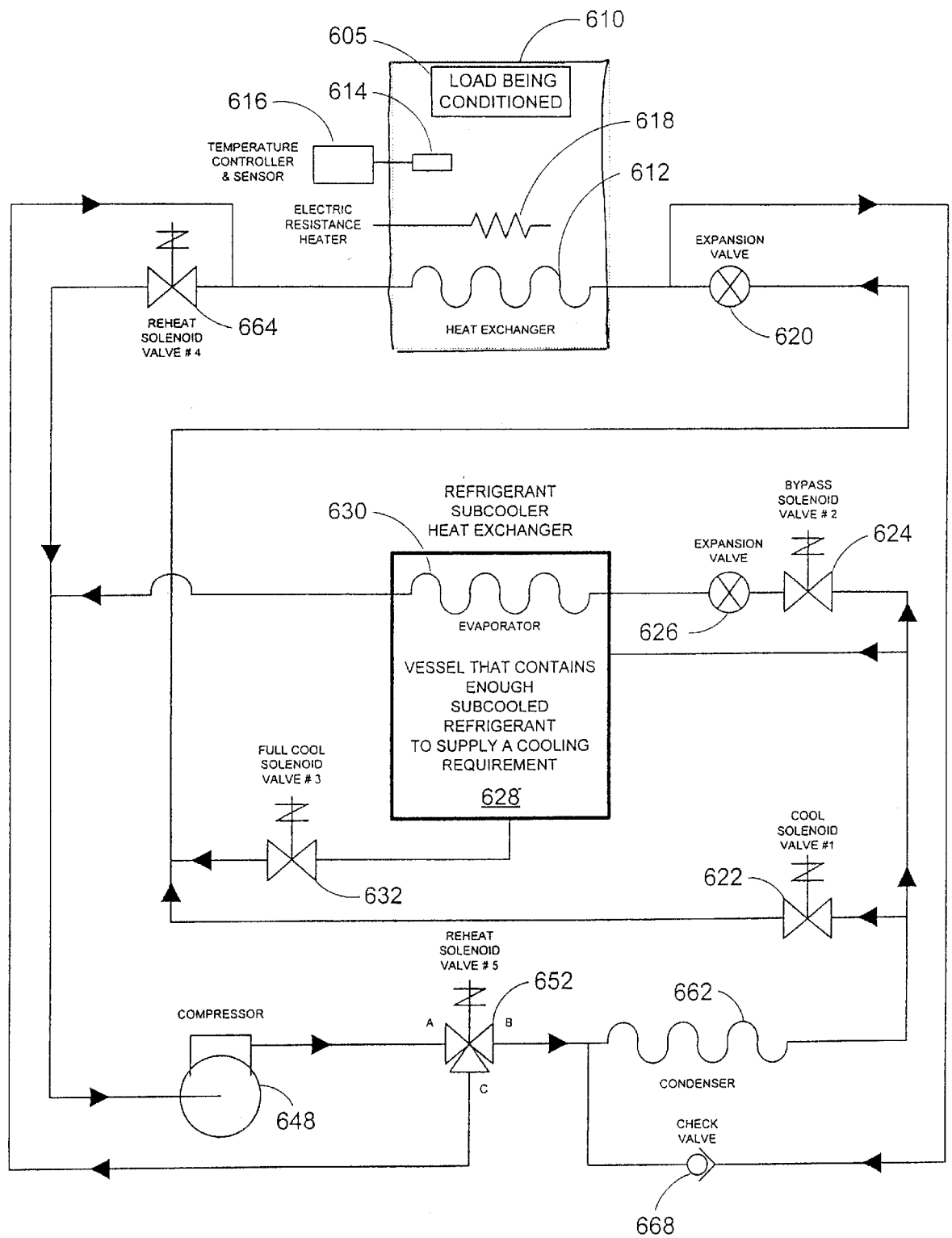
FIG. 8 is a conceptual block diagram of a fourth embodiment of the present invention utilizing a non-cascade refrigeration and heating system and thermal storage of subcooled refrigerant.

Referring to FIG. 8, a conceptual block diagram of another embodiment of the present invention utilizing a non-cascade refrigeration and heating system and thermal storage of subcooled refrigerant is shown ("the system 600" hereinafter). The system 600 comprises only one refrigeration sub-system. The refrigeration sub-system comprises a plurality of paths for the different cooling and heating operations of the system 600. The general construction and operation of the system 600 us described below. As an aid, the solenoid valve positions for the desired system 600 operations are summarized in table 3 as shown in FIG. 11.

The system 600 initial conditions are:

1. The refrigeration sub-system is running. It should be noted that while not shown herein, other required equipment such as fans, control equipment etc. is also functional.
2. The thermal storage unit 628 (subcooler 628) has already been cooled, the refrigerant within being sub-cooled.
3. The load being temperature conditioned 605 is warmer than the desired target temperature at the end of the conditioning cycle.
4. The refrigeration and heating system contains refrigerant R-507.
5. A PID (Proportional-Integral-Derivative) programmable temperature controller 616 is being used to control the position of the solenoid valves 622, 624, 632, 664, and 652.
6. Electric resistance heaters 618 used for heating are off.

Cooldown Cycle

At the start of a cooldown cycle, the temperature controller 616 signals for full cooling and opens solenoid valves #3 632 and #4 664; and simultaneously closes solenoid valves #1 622 and #2 624 to which the temperature controller 616 is coupled. Subcooled refrigerant R-507 flows from the subcooler 628 through solenoid valve #3 632, and through expansion valve 620. The refrigerant R-507 then enters the heat exchanger coil 612, integral to the environmental test chamber 610 to cool the load being conditioned 605. The refrigerant R-507 is vaporized while passing through the heat exchanger coil 612 due to absorbing heat from the load being conditioned 605. The discharge from the heat exchanger coil 612 is through solenoid valve #4 664 to the suction of the compressor 648 where the refrigerant R-507 is compressed. Once the refrigerant R-507 is compressed, it travels through solenoid valve #5 652, port A to B, to the condenser coil 662 for removal of heat and condensing back into a liquid. The refrigerant R-507 then travels back into the subcooler 628. This completes the refrigerant R-507 flowpath during the full cool, or cooldown, cycle of the system 600.

Cooldown Maintaining Cycle

When the desired setpoint of the load being conditioned 605 is reached, the temperature controller 616 starts to throttle the cooling to maintain temperature at the desired setpoint. The temperature controller 616 proportions solenoid valve #1 622 on a timed cycle to maintain the desired temperature at the heat exchanger coil 612 as sensed by the sensor 614. When the demand for cooling is less than 100% the temperature controller 616 maintains solenoid valve #4 664 open and closes solenoid valve #3 632. The temperature controller 616 continues to proportion solenoid valve # 1 622 on a timed cycle to maintain the desired temperature of the heat exchanger coil 612 and thus the load being conditioned 605. This is the cooldown maintaining cycle of the system 600.

Heat up Cycle

When a temperature increase, or heat up cycle, is desired the temperature controller 616 energizes the electric resistance heaters 618. The temperature controller 616 opens solenoid valves #2 624, and closes solenoid valves #1 622, #3 632 and #4 664. The temperature controller 616 causes solenoid valve #5 652 to change the position of its ports. Port A is opened to port C, and port B is blocked so that refrigerant R-507 hot gas flows from the compressor 648 to the heat exchanger coil 612, integral to the environmental test chamber 610, as a high-pressure hot gas, heating the load being conditioned 605. The refrigerant R-507 then travels through the check valve 668 and through the condenser coil 662 to be condensed, then through solenoid valve #2 624 and into the evaporator coil 630, integral to the subcooler 628, subcooling the stored liquid R-507. Then the refrigerant R-507 travels back to the compressor 648 to be compressed again. This begins the cool down of the subcooler 628 for the next cooling cycle. And importantly it keeps a load on the refrigeration and heating system 600. This completes the heating cycle of refrigerant R-507.

Heat up Maintain/Subcool Cycle

At a predetermined temperature and/or heating demand the temperature controller 616 causes solenoid valve #5 652 to change the position of it's ports. Port A is opened to port B, and port C is blocked so that refrigerant R-507 continues to flow to the condenser coil 662. The heating process of the load being conditioned 605 continues with only the electric resistance heaters 618 cycling as controlled by the temperature controller 616 and the temperature sensor 614. Solenoid valve #2 624 remains open during this time to continue the process of subcooling the stored liquid refrigerant R-507 in the subcooler 628 for the next cooldown cycle.

An important feature of the present invention, in all embodiments, is the thermal storage unit which is the subcooler 328, 428, 528, and 628. The thermal storage unit in one embodiment comprises a shell and tube heat exchanger for storing subcooled refrigerant for the next cooldown cycle. The shell of the subcooler 328, 428, 528, and 628 has enough volume to hold the required amount of refrigerant for the cooling performance enhancement needed as well as for the heating enhancement needed. In the cascade refrigeration and heating system embodiments 300, 400, and 500, a brazed plate heat exchanger serves as the secondary subcooler #2 334, 434, and 534.

While the invention has been particularly shown and described with reference to the preferred embodiments thereof, it will be understood by those skilled in the art that the foregoing and other changes in form, and details may be made therein without departing from the spirit and scope of the invention.

What is claimed is:

1. A refrigeration system having fast cool down and heat up phases, said refrigeration system comprising in combination;
   a) an environmental test chamber for providing fast cool down and heat up phases for an object(s) under test;
   b) a heat exchanger coupled with said test chamber;
   c) a thermal storage unit for providing a supply of subcooled refrigerant;
   d) an expansion valve for metering liquid refrigerant flowing from said thermal storage unit and through said heat exchanger to draw heat from said test chamber and cool the objects(s) therein during the fast cool down phase;
   e) a compressor for compressing the gaseous refrigerant received from said heat exchanger during the fast cool down phase;
   f) a condenser for transforming the gaseous refrigerant to a liquid refrigerant to cool the liquid refrigerant prior to conveying the liquid refrigerant to said thermal storage unit during the fast cool down phase;
   g) a temperature sensor and controller for sensing the temperature of said test chamber and for actuating elements of said refrigeration system;
   h) a valve under control of said temperature sensor and controller as a function of a pre set temperature for said test chamber for selectively bypassing flow of refrigerant into said thermal storage unit during the fast cool down phase;
   i) a further valve for directing gaseous refrigerant from said compressor to said heat exchanger during the fast heat up phase;
   j) said condenser being coupled with said heat exchanger to receive the refrigerant from said heat exchanger during the fast heat up phase;
   k) an expansion valve for cooling the refrigerant received from said condenser prior to conveying the cooled refrigerant to a further heat exchanger coupled with said thermal storage unit during the fast heat up phase;
   l) a conduit for conveying refrigerant from said further heat exchanger to said compressor during the fast heat up phase; and
   m) a heater under control of said temperature sensor and controller and coupled with said test chamber for augmenting a rapid temperature rise within said test chamber during the fast heat up phase.

2. The refrigeration system of claim 1 including a yet further valve for transmitting subcooled refrigerant from said thermal storage unit to said expansion valve only during the fast cool down phase in response to said temperature sensor and controller.

3. The refrigeration system of claim 1 wherein the range of temperature excursion provided within said test chamber absent actuation of said heater is from about ambient temperature to about −50° F.

* * * * *